(12) United States Patent
Fassbender et al.

(10) Patent No.: US 10,562,835 B1
(45) Date of Patent: Feb. 18, 2020

(54) METHOD FOR PRODUCING THORIUM-226

(71) Applicants: Michael E. Fassbender, Los Alamos, NM (US); Tara E. Mastren, Los Alamos, NM (US)

(72) Inventors: Michael E. Fassbender, Los Alamos, NM (US); Tara E. Mastren, Los Alamos, NM (US)

(73) Assignee: Triad National Security, LLC, Los Alamos, NM (US)

( * ) Notice: Subject to any disclaimer, the term of this patent is extended or adjusted under 35 U.S.C. 154(b) by 0 days.

(21) Appl. No.: 15/954,924

(22) Filed: Apr. 17, 2018

Related U.S. Application Data

(60) Provisional application No. 62/487,694, filed on Apr. 20, 2017.

(51) Int. Cl.
| | |
|---|---|
| *C07C 51/41* | (2006.01) |
| *A61K 51/10* | (2006.01) |
| *B01J 39/05* | (2017.01) |
| *B01D 59/30* | (2006.01) |
| *G21G 1/00* | (2006.01) |
| *B01J 39/19* | (2017.01) |

(52) U.S. Cl.
CPC .......... *C07C 51/418* (2013.01); *B01D 59/30* (2013.01); *B01J 39/05* (2017.01); *B01J 39/19* (2017.01); *G21G 1/0005* (2013.01); *G21G 2001/0094* (2013.01)

(58) Field of Classification Search
CPC ................................ C07C 51/41; A61K 51/00
See application file for complete search history.

(56) References Cited

U.S. PATENT DOCUMENTS 7,794,691 B2 * 9/2010 Morgenstern ...... A61K 51/1045
424/1.11

OTHER PUBLICATIONS

Alhassanieh et al., "Separation of Th, U, Pa, Ra and Ac from natural uranium and thorium series," *Applied Radiation and Isotopes* 51:493-498, Jul. 23, 1999.
Carswell, "Separation of thorium and uranium nitrates by anion exchange," *Journal of Inorganic and Nuclear Chemistry* 3(6):384-387, Jan. 1957.
Carter et al., "Determination of uranium and thorium in geological materials using extraction chromatography," *Analyst* 124:271-274, Jan. 1999.
Dahle et al., "Initial Evaluation of $^{227}$Th-p-benzyl-DOTA-rituximab for low-dose rate α-particle radioimmunotherapy," *Nuclear Medicine and Biology* 33:271-279, Feb. 2006.
Dahle et al., "In Vitro cytotoxicity of low-dose-rate radioimmunotherapy by the alpha-emitting radioimmunoconjugate Thorium-227-Dota-rituximab," *International Journal of Radiation Oncology* 75(3):886-895, Aug. 11, 2009.

Deorkar et al., "Separation of uranium(Vi) as chloride complex by solvent-extraction with dicyclohexyl-18-crown-6," *Journal of Radioanalytical and Nuclear Chemistry* 130(2):433-441, Apr. 1989.
Hendriksen et al., "Thorium and Actinium Polyphosphonate Compounds as Bone-seeking Alpha Particle-emitting Agents," *Anticancer Research* 24:101-105, Jan. 2004.
Jacques et al., "Kinetically and thermodynamically stable isomers of thorium chelates of polyaza polycarboxylic macrocycles," *Journal of Alloys and Compounds* 213-214:286-289, Oct. 1994.
Korkisch et al., "Anion exchange separation of uranium, thorium and bismuth," *Fresenius' Zeitschrift für analytische Chemie* 186(2):290-295, Jun. 1962.
Korkisch et al., "Application of ion-exchange separations to determination of trace elements in natural waters—IX Simultaneous isolation and determination of uranium and thorium," *Talanta* 23(4):295-300, Apr. 1976.
Pathak et al., "Separation Studies of Uranium and Thorium Using Di-2-Ethylhexyl Isobutyramide (D2EHIBA)," *Separation Science and Technology* 34(13):2601-2614, Sep. 1999.
Peppard et al., "The mutual separation of thorium, protoactinium, and uranium by tributyl phosphate extraction from hydrochloric acid," *Journal of Inorganic and Nuclear Chemistry* 3(6):370-378, Jan. 1957.
Pham et al. "A Macrocyclic Chelator with Unprecedented Th$^{4+}$ Affinity," *Journal of the American Chemical Society* 136(25):9106-9115, May 2014.
Radchenko et al., "Application of ion exchange and extraction chromatography to the separation of actinium from proton-irradiated thorium metal for analytical purposes," *Journal of Chromatography A* 1380:55-63, 2015; Published online Dec. 18, 2014.
Radchenko et al., "Formation cross-sections and chromatographic separation of protactinium isotopes formed in proton-irradiated thorium metal," *Radiochimica Acta* 104(5):291-304, Jan. 12, 2016.
Raju et al., "Sequential separation of lanthanides, thorium and uranium using novel solid phase extraction method from high acidic nuclear wastes," *Journal of Hazardous Materials* 145(1-2):315-322, Jun. 2007.
Ramdahl et al., "An efficient chelator for complexation of thorium-227," *Bioorganic & Medicinal Chemistry Letters* 26(17):4318-4321, Sep. 2016; published online Jul. 17, 2016.
Seyhan et al., "Use of o-phenylene dioxydiacetic acid impregnated in Amberlite XAD resin for separation and preconcentration of uranium(VI)and thorium (IV)," *Journal of Hazardous Materials* 152(1):79-84, Mar. 2008, published online Jun. 23, 2007.

(Continued)

*Primary Examiner* — Michael G. Hartley
*Assistant Examiner* — Jagadishwar R Samala
(74) *Attorney, Agent, or Firm* — Klarquist Sparkman, LLP

(57) ABSTRACT

Disclosed herein are embodiments of a method for producing thorium-226. The method comprises separating thorium-226 from uranium-230 to produce a solution of thorium-226 in a solvent, such as a chelating buffer, suitable for direct labeling by a chelate. The thorium-226 may be separated from the uranium-230 using extraction chromatography. The extraction may be repeated multiple times as additional thorium-226 is produced by uranium-230 decay.

19 Claims, 7 Drawing Sheets

(56) References Cited

OTHER PUBLICATIONS

Sharma et al., "Separation studies of uranium and thorium using tetra(2-ethylhexyl) diglycolamide (TEHDGA) as an extract," *Journal of Radioanalytical and Nuclear Chemistry* 278(1):173-177, Oct. 2008, published online Jun. 3, 2008.

Yokoyama et al., "Separation of thorium and uranium from silicate rock samples using two commercial extraction chromatographic resins," *Analytical Chemistry* 71(1):135-141, Nov. 1999.

\* cited by examiner

METHOD FOR PRODUCING THORIUM-226

CROSS REFERENCE TO RELATED APPLICATION

This application claims the benefit of the earlier filing date of U.S. Provisional Application No. 62/487,694, filed Apr. 20, 2017, which is incorporated herein by reference in its entirety.

ACKNOWLEDGMENT OF GOVERNMENT SUPPORT

This invention was made with government support under Contract No. DE-AC52-06NA25396 awarded by the U.S. Department of Energy, and under Grant No. FOA LAB 14-1099 awarded by the U.S. Department of Energy, Office of Science. The government has certain rights in the invention.

FIELD

This disclosure concerns the production of thorium-226 from uranium-230.

BACKGROUND

The use of radioactive decay to treat cancer has been a widely used method in cancer treatment since its discovery. However, many such treatment methods involve the irradiation of the general area of the cancer, thus potentially causing harm to healthy tissues in the process. Targeted therapy is an emerging field of research where therapeutic radioisotopes are delivered directly to the cancer cells of interest by attaching them to a targeting moiety (ligand, small molecule, or protein) that has a high affinity for the cancer cells being targeted. Targeted alpha therapy (TAT) is the use of isotopes that decay by emitting α-particles, and is of particular interest because α-emission is associated with a high linear energy transfer (LET), meaning suitable emitters can deliver a large radiation dose to tissue within a short range (about 100 µm). Thus, the majority of the damage occurs within the cancer cells with a minimal impact to the surrounding healthy tissue.

Thorium-226 ($^{226}$Th) is an isotope of interest for targeted alpha therapy. It has a half-life of 30.6 minutes and decays via a four alpha decay chain to long-lived lead-210 ($^{210}$Pb), which has a half-life of 22.3 years. Thorium-226 emits a 111 keV gamma-ray (3.29%) that can be used for single-photon emission computed tomography (SPECT) imaging, thus providing theranostic capabilities. Due to the relatively short half-life of $^{226}$Th, a generator is useful to provide a consistent supply of this isotope from its parent uranium-230 ($^{230}$U), which has a half-life of 20.23 days.

Several separation strategies have been researched and developed for the separation of uranium and thorium. These separation methods involve the use of solvent extraction, solid phase extraction, and anion exchange chromatography. However, these approaches include the use of strong acids that would denature any peptides or proteins that were labeled with the $^{226}$Th. Consequently, the $^{226}$Th eluent has to be treated (via evaporation or pH adjustment) prior to being suitable for chelation reactions. The amount of time lost in this process, which typically requires at least one $^{226}$Th half-life of radiochemical operation (i.e. about 30 minutes), is disadvantageous for providing high radiochemical yields.

SUMMARY

Eluting $^{226}$Th in a form that is amenable to direct labeling with the chelate minimizes the time required for chelate and bioconjugate preparation and is beneficial to providing a radiolabeled compound with minimal loss of activity. Disclosed herein are embodiments of a method for making a supply of $^{226}$Th in a carboxylate based chelating buffer, such as 0.1 M citric acid, from a $^{230}$U/$^{226}$Th generator. By using a chelating buffer, the $^{226}$Th is immediately available for chelation to macrocyclic chelators, including, but not limited to, 1,4,7,10-tetraazacyclododecane-1,4,7,10-tetraacetic acid (DOTA), 1,4,7-triazacyclononane-1,4,7-triacetic acid (NOTA), 1-(1,3-carboxypropyl)-1,4,7-triazacyclononane-4.7-diacetic acid (NODAGA), 1,4,7,10,13,16-hexaazacyclohexadecane-N,N',N'',N''',N'''',N'''''-hexaacetic acid (HEHA) 1,4,7,10,13-pentaazacyclopentadecane-N,N',N'', N''',N''''-pentaacetic acid (PEPA), desferoxamine (DFO) or peptides and/or proteins.

In some embodiments, the method comprises forming a first solution comprising uranium-230 and thorium-226, contacting a first resin with the first solution such that the uranium-230 and the thorium-226 bind to the first resin, and forming a second solution comprising thorium-226 and a chelating buffer, such as a carboxylic acid-based chelating buffer. The first solution may comprise a first mineral acid, for example, hydrochloric acid, hydrofluoric acid, hydrobromic acid, hydriodic acid, sulfuric acid, nitric acid, phosphoric acid, or a combination thereof. In certain embodiments, the first mineral acid is or comprises hydrochloric acid. Additionally, or alternatively, the first mineral acid may have a concentration of from greater than 2 M to 12 M, such as from 4 M to 10 M, and in certain embodiments, the first acid concentration is 6 M.

The first resin may be a diglycolamide resin, a monoamide resin, a malonamide resin, a multi-podant DGA ligand, a phosphonic acid resin, a phosphine oxide resin, or a phosphine sulfide resin. In certain embodiments, the resin is a diglycolamide resin, such as N,N,N',N'-tetra-n-octyldiglycolamide, or N,N,N',N'-tetrakis-2-ethylhexyldiglycolamide. In certain other embodiments, the resin is a phosphonic acid resin, a phosphine sulfide resin, or a phosphine oxide resin, such as octylphenyl-N,N-di-isobutyl carbamoylphosphine oxide.

The method may further comprise separating the uranium-230 from the first resin to form a third solution, before forming the second solution comprising the thorium-226. A person of ordinary skill in the art will appreciate that even when substantially all of a metal is separated from a resin, there might be trace amounts of the metal remaining on the resin, such as less than 0.5%, less than 0.2%, less than 0.1%, or less than 0.01%. Separating the uranium-230 from the first resin may comprise eluting the uranium-230 from the first resin with a first eluent. The first eluent may be an aqueous acid, such as a second mineral acid, and/or may be nitric acid, hydrochloric acid, hydrobromic acid, hydriodic acid, hydrofluoric acid, sulfuric acid, phosphoric acid, or a combination thereof, typically nitric acid. Additionally, or alternatively, the first eluent may have a second acid concentration of from greater than zero to less than 6M, such as from greater than zero to 3 M, or from 0.01 M to 0.25 M, and in some examples, the second acid concentration is 0.1 M. In some embodiments, the second mineral acid is different from the first mineral acid and/or has a different acid concentration.

The method may further comprise allowing the third solution to stand for a time period sufficient for a portion of the uranium-230 in the third solution to decay to form additional thorium-226, adding the third solution to the first resin, and eluting the additional thorium-226 with an additional amount of the chelating buffer. The time period may be from 30 to 360 minutes, or the time period may be about ten thorium-226 half-lives. A third mineral acid may be added to the third solution to increase an acid concentration of the third solution to at least 6M, such as from 6M to 12M. The third mineral acid may be hydrochloric acid, hydrofluoric acid, hydrobromic acid, hydriodic acid, sulfuric acid, nitric acid, phosphoric acid, or a combination thereof, and may be the same as the first mineral acid.

In some embodiments, forming the second solution comprising the thorium-226 comprises eluting the thorium-226 from the first resin with the chelating buffer. In other embodiments, including embodiments where the resin is a phosphonic acid resin, phosphine oxide resin, or a phosphine sulfide resin, forming the second solution comprises eluting the thorium-226 from the first resin with a fourth acid to form a fourth solution, contacting a cation exchange resin with the fourth solution, and separating the thorium-226 from the cation exchange resin to form the second solution. Separating the thorium-226 from the cation exchange resin may comprise eluting the thorium-226 from the cation exchange resin with the chelating buffer to form the second solution. The fourth acid may be a fourth mineral acid, such as hydrochloric acid, hydrofluoric acid, hydrobromic acid, hydriodic acid, sulfuric acid, nitric acid, phosphoric acid, or a combination thereof, typically hydrochloric acid. The fourth acid may have a fourth acid concentration of from 0.5 M to 4 M. And/or the cation exchange resin may be an acidic resins, such as a Bio-rad AG® 50 W or Bio-rad AG® MP-50 strongly acidic resins, or Dowex® 50WX, such as Dowee® 50WX8, or Dionex™ cation exchange resins.

The method may further comprise allowing the first resin and uranium-230 to stand for a time period sufficient for a portion of the uranium-230 on the first resin to decay to form additional thorium-226, and eluting the additional thorium-226 from the first resin with an additional amount of the chelating buffer. The time period may be from 30 to 360 minutes, or about 10 thorium-226 half-lives.

In any embodiments, the chelating buffer may be selected to facilitate direct chelation of the thorium-226 in the chelating buffer by a therapeutic and/or diagnostic chelating molecule. The chelating buffer may be a carboxylic acid-based chelating buffer and/or may comprise a carboxylic acid. The carboxylic acid may comprise a hydroxyl group and/or multiple carboxyl moieties, such as 2, 3, 4, 5, or 6 carboxyl moieties. In some embodiments, the chelating buffer comprises, consists essentially of, or consists of, glycolic acid, citric acid, tartaric acid, malonic acid, oxalic acid, succinic acid, glutaric acid, adipic acid, isocitric acid, aconitric acid, propane-1,2,3-tricarboxylic acid, malic acid, maleic acid, lactic acid, or a combination thereof, preferably citric acid. The chelating buffer may have a pH of from 0 to 8, such as from 2 to 6, or from 4 to 6, and in some embodiments, the pH is 5.

In certain embodiments, the method comprises forming a first solution comprising uranium-230 and thorium-226 in 6M hydrochloric acid, contacting a diglycolamide resin with the first solution to bind the uranium-230 and thorium-226 to the resin, eluting the uranium-230 from the resin with nitric acid having a nitric acid concentration of from 0.01 M to 0.25 M, to form a second solution comprising uranium-230, and eluting the thorium-226 from the resin with a chelating buffer to form a third solution comprising thorium-226, where the chelating buffer comprises a carboxylic acid and has a pH of from 2 to 6. The chelating buffer may be citric acid, and/or the nitric acid concentration may be 0.1 M.

In other embodiments, the method comprises forming a first solution comprising uranium-230 and thorium-226 in 6M hydrochloric acid, contacting a phosphine oxide resin, a phosphonic acid resin, or a phosphine sulfide resin with the first solution to bind the uranium-230 and thorium-226 to the resin, eluting the thorium-226 from the resin with a first portion of hydrochloric acid, optionally having a hydrochloric acid concentration of from 0.5 M to 4 M, to form a second solution comprising thorium-226. The method also comprises contacting a cation exchange resin with the second solution, and eluting the thorium-226 from the cation exchange resin with a chelating buffer to form a third solution comprising thorium-226, where the chelating buffer comprises a carboxylic acid, such as citric acid, and has a pH of from 4 to 6. The method may further comprise allowing the phosphonic acid resin, phosphine oxide resin, or phosphine sulfide resin to stand for 5 hours, and eluting a second portion of thorium-226 from the phosphonic acid, phosphine oxide or phosphine sulfide resin with a second portion of hydrochloric acid to form a fourth solution.

In any embodiments of the disclosed method, the radiochemical yield of thorium-226 may be from 50% to 99.9%, such as from 85% to 95%. Additionally, or alternatively, the thorium-226 in the third solution may have a radiochemical purity of from 80% to 100%, such as from 99% to 100%.

The foregoing and other objects, features, and advantages of the invention will become more apparent from the following detailed description, which proceeds with reference to the accompanying figures.

DETAILED DESCRIPTION

I. Definitions

The following explanations of terms and abbreviations are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. Other features of the disclosure are apparent from the following detailed description and the claims.

Unless otherwise indicated, all numbers expressing quantities of components, molecular weights, percentages, temperatures, times, and so forth, as used in the specification or claims are to be understood as being modified by the term "about." Accordingly, unless otherwise indicated, implicitly or explicitly, the numerical parameters set forth are approximations that may depend on the desired properties sought and/or limits of detection under standard test conditions/methods. When directly and explicitly distinguishing embodiments from discussed prior art, the embodiment numbers are not approximates unless the word "about" is recited.

"Loading Breakthrough" refers to the amount of $^{230}$U that is eluted while the column is being loaded and before formal elution begins.

"Radiochemical yield" refers to the yield of a desired isotope from a radiochemical separation of isotopes, expressed as a fraction of the activity due to the desired isotope that was originally present.

"Radiochemical purity" refers to the fraction of the total activity of the stated isotope present in the stated chemical form.

II. Method for Producing Thorium-226 from Uranium-230

Figure 1:
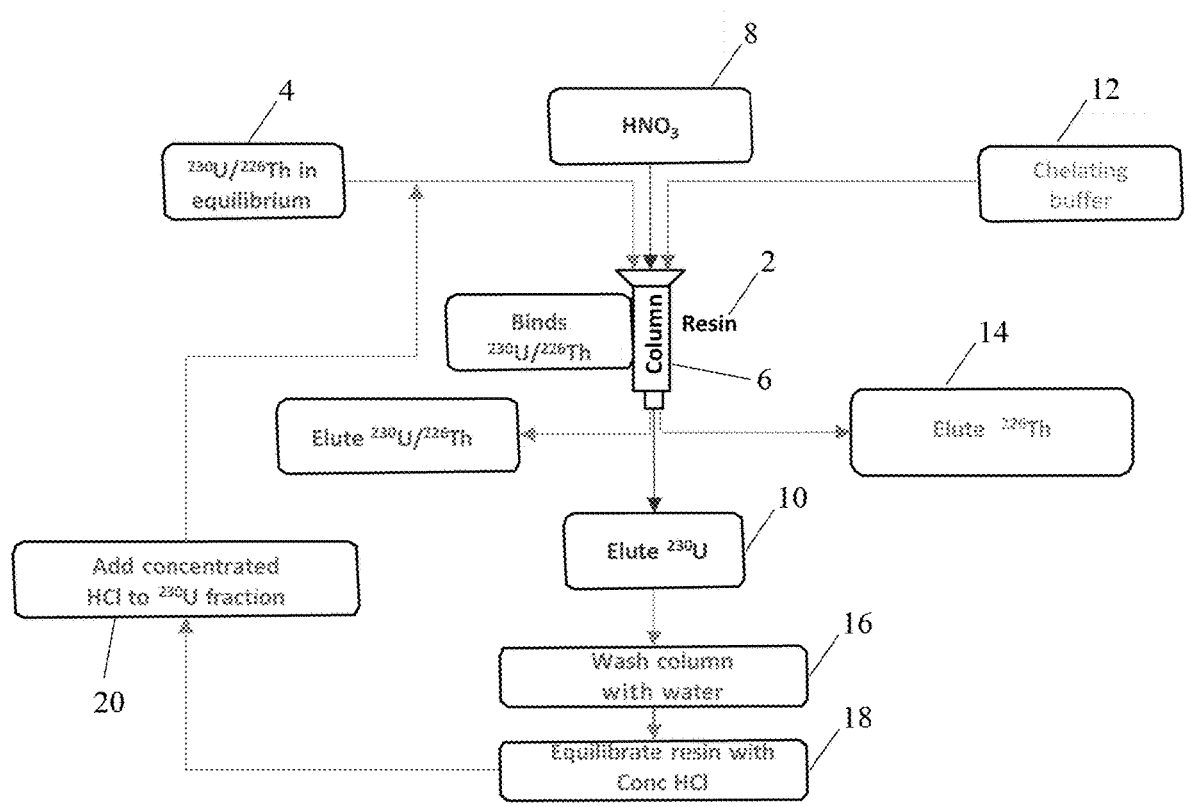
FIG. 1 is a flow chart describing one exemplary embodiment of the method.

The method for producing $^{226}$Th comprises separating $^{226}$Th from its parent isotope $^{230}$U. The $^{230}$U may be prepared from one of its parent isotopes, such as protactinium-230 ($^{230}$Pa), by a suitable technique such as extraction chromatography. FIG. 1 provides a flow chart of an exemplary embodiment of the disclosed method. With reference to FIG. 1, an extraction chromatography resin 2 is contacted with mixture 4 comprising $^{230}$U and $^{226}$Th. The $^{230}$U and $^{226}$Th may be in equilibrium, that is where the amount of $^{226}$Th that is decaying is substantially, or quantitatively exactly, being replaced by $^{226}$Th that is being produced by $^{230}$U decay, and accordingly the amount of $^{226}$Th is at an approximate steady state. In some embodiments, when the $^{230}$U and $^{226}$Th are in equilibrium the radioactivity due to the $^{226}$Th is substantially the same as the radioactivity due to the $^{230}$U.

The mixture 4 of $^{230}$U and $^{226}$Th may be a solution, such as an acidic solution. The acidic solution may comprise a mineral acid, such as hydrochloric acid, hydrofluoric acid, hydrobromic acid, hydriodic acid, sulfuric acid, nitric acid, phosphoric acid, or a combination thereof. In some embodiments, hydrochloric acid is used. A suitable concentration of the acid is used to ensure that the uranium and thorium binds to the resin. The concentration may be from greater than 2 M to 12 M or more, from 3 M to 12 M, from 4 M to 12 M, or from 6 M to 10 M. In some embodiments, a concentration of 6M or more, such as from 6M to 12M, is used, and in certain examples, 6M hydrochloric acid is used.

The extraction chromatography resin 2 may be any chromatography resin suitable to separate $^{226}$Th from $^{230}$U. The extractant is present either in the form of a solution-impregnated resin or grafted to the resin. The extractant may be impregnated on the resin ("extraction chromatography resin") in the form of a solution containing the extractant, such as a diglycolamide, in a molecular solvent or covalently bonded (grafted) to the resin. The resin may be a diglycolamide resin, monoamide resin, malonamide resin, phosphonic acid resin, phosphine oxide resin, phosphine sulfide resin, or a multi-podant DGA ligand. In certain embodiments, a diglycolamide resin is used, such as N,N,N',N'-tetra-n-octyldiglycolamide (DGA Resin, Normal, Eichrom, USA) or N,N,N',N'-tetrakis-2-ethylhexyldiglycolamide (DGA Resin, Branched, Eichrom, USA). In other examples, phosphonic acid, phosphine oxide or phosphine sulfide resin is used, such as octylphenyl-N,N-di-isobutyl carbamoyl-phosphine oxide (TRU resin, Eichrom, USA; CL resin, TrisKem, France).

The resin may be in any form suitable to facilitate separation of the $^{226}$Th from the $^{230}$U. In some embodiments, the resin is used as a solid for solid supported liquid/liquid extraction, such as in a column 6. For solid supported liquid/liquid extraction, the resin may be washed with purified water, such as milli-Q water, and/or equilibrated with a mineral acid or acids, before the mixture of $^{230}$U and its decay product $^{226}$Th is sorbed onto it. Typically, the mineral acid(s) is the same mineral acid(s) that is used to dissolve the $^{230}$U/$^{226}$Th mixture. In some embodiments, concentrated hydrochloric acid is used to equilibrate the resin. The water and mineral acid, such as hydrochloric acid, may be in a ratio of about 10:1.

With respect to FIG. 1, after sorption onto the resin 2, typically a diglycolamide resin, the $^{230}$U is eluted by a suitable elution solvent 8 to form an acidic solution 10 of $^{230}$U. Suitable elution solvents include mineral acids, such as hydrochloric acid, hydrofluoric acid, hydrobromic acid, hydriodic acid, sulfuric acid, nitric acid, phosphoric acid, or a combination thereof. In some embodiments, nitric acid or hydrochloric acid is used, preferably nitric acid. The concentration of the elution solvent is suitable to facilitate elution of the $^{230}$U while $^{226}$Th substantially remains sorbed on column 6. In some embodiments, the elution solvent concentration used is below 6M, such as from greater than zero to less than 6M, from greater than zero to 3 M, greater than zero to 2 M, greater than zero to 1 M, greater than zero to 0.5 M, from 0.01 M to 0.25 M or from 0.05 M to 0.2 M. In certain examples, 0.1 M nitric acid is used.

After elution of the $^{230}$U, the $^{226}$Th is eluted in a separate elution step, using a chelating buffer 12 to form a solution 14 of $^{226}$Th in the chelating buffer 12. The chelating buffer 12 can be any buffer suitable to chelate and elute the $^{226}$Th from the resin. In some embodiments, the chelating buffer 12 comprises a carboxylic acid. The carboxylic acid may comprise at least one hydroxyl (—OH) moiety and/or more than one carboxyl moiety (—CO$_2$H), such as 2, 3, 4, 5, 6, or more carboxyl moieties. Suitable carboxylic acids include, but are not limited to glycolic acid, citric acid, tartaric acid, malonic acid, oxalic acid, succinic acid, glutaric acid, adipic acid, isocitric acid, aconitric acid, propane-1,2,3-tricarboxylic acid, malic acid, maleic acid, lactic acid, or a combination thereof. In certain embodiments, the chelating buffer 12 comprises citric acid. The chelating buffer 12 may also comprise a base suitable to buffer the solution in a desired pH range. Exemplary bases include, but are not limited to, hydroxide bases, such as sodium hydroxide, potassium hydroxide, lithium hydroxide, calcium hydroxide or a combination thereof. Additionally, or alternatively, a chelating buffer 12 may comprise an acid and its conjugate base, for example, citric acid and a citrate salt, such as sodium citrate.

In some embodiments, the pH of the chelating buffer 12 is selected to facilitate elution of the $^{226}$Th. The pH may be from 0 or less to 8 or more, such as from 1 to 8, from 2 to 8, or from 2 to 6, or from 5 to 6, and in some examples, a pH of 5 is used.

A suitable concentration of the chelating buffer 12 is used to facilitate $^{226}$Th elution. The concentration may be from greater than zero to 0.5 M or more, such as from 0.01 M to 0.25 M, or from 0.05 M to 0.2 M, and in some examples, a 0.1 M concentration of chelating buffer 12 is used. In some embodiments, the chelating buffer 12 comprises 0.1 M citric acid at pH 5, and in certain disclosed embodiments, the chelating buffer 12 comprises 0.1 M citric acid buffered with sodium hydroxide at pH 5.

After elution of the $^{226}$Th, the resin is washed water 16, such as milli-Q water, and equilibrated with a suitable concentration of mineral acid 18 as previously described for the preparation of the resin for solid/liquid extraction. Meanwhile, the acidic solution 10 of $^{230}$U is allowed to stand to produce more $^{226}$Th by radioactive decay of the $^{230}$U. The acidic solution 10 may be allowed to stand until the $^{226}$Th again achieves equilibrium with the $^{230}$U. Alternatively, the acidic solution 10 may be allowed to stand for a period of time of from 5 to 12 or more $^{226}$Th half-lives (about 30 to 360 minutes), such as from 7 to 12 half-lives (214 to 360 minutes), or from 8 to 11 half-lives (244 to 330 minutes), or about 10 half-lives (about 306 minutes or 5 hours), where a $^{226}$Th half-life is about 30.6 minutes.

An amount of mineral acid is then added to the acidic solution 10 to form an acid solution 20 having an acid concentration of at least 6 M. Optionally, the concentration of the resulting solution 20 is substantially the same acid concentration as was used to prepare the original $^{230}$U/$^{226}$Th solution. The mineral acid that is added may be the same mineral acid that was previously used to make the $^{230}$U/$^{226}$Th solution. In some embodiments, an equal volume of concentrated hydrochloric acid is added. The resulting solution 20 is then passed through the resin to re-sorb the $^{230}$U and $^{226}$Th onto the resin. The elution process is then repeated one or more times, such as 1, 2, 3, 4, 5 or more times, to separate the $^{226}$Th from the $^{230}$U and form solutions of $^{226}$Th in the chelating buffer. In some embodiments, the elution process is performed once or twice daily, and may be performed for up to 10 half-lives of $^{230}$U, such as about 200 days.

Figure 2:
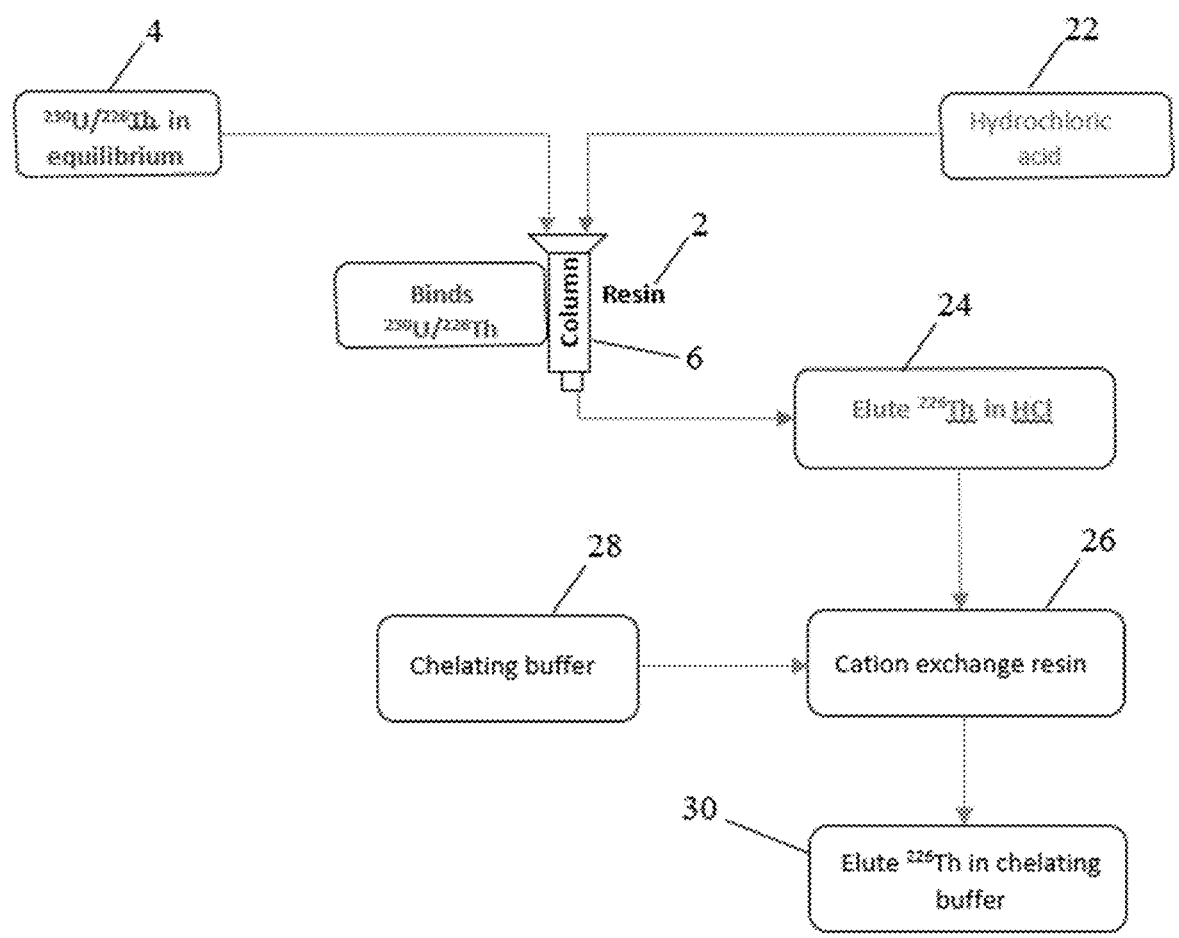
FIG. 2 is a flow chart describing an alternative embodiment of the method.

In alternative embodiments, and with reference to FIG. 2, the resin 2 may be a phosphonic acid resin, phosphine oxide resin, or a phosphine sulfide resin. The resin 2 is contacted with the solution 4, as previously described, to bind the uranium-230 and thorium-226 to the resin. The thorium-226 is then eluted from the resin 2 with an acid suitable to elute the thorium-226 to form solution 24, while substantially leaving the uranium-230 on the resin. The acid may be a mineral acid, such as hydrochloric acid, hydrofluoric acid, hydrobromic acid, sulfuric acid, nitric acid, phosphoric acid, or a combination thereof, and in some embodiments is hydrochloric acid. The acid may have an acid concentration suitable to facilitate substantially selective elution of thorium-226, such as from 0.5 M to 10 M, from 0.5 M to 6M, or from 0.5 M to 4 M, and in some examples, 2 M is used.

In certain embodiments, the method further comprises adding the solution 24 to a cation exchange resin 26 to re-sorb the $^{226}$Th. The thorium-226 is then eluted with a chelating buffer 28 to form a solution 30 comprising thorium-226 in the chelating buffer. Suitable cation exchange resins include any resin that facilitates exchange of the thorium-226 from the acid solution 24 to a chelating buffer, such as Bio-rad AG® 50 W or AG® MP-50 type strongly acidic resins, DOWEX® or Dionex™ cation exchanger resins. The chelating buffer 28 can be any chelating buffer suitable to elute the thorium-226 from the resin, such as the chelating buffers previously described with respect to FIG. 1. In some embodiments, the chelating buffer comprises a carboxylic acid. The chelating buffer may comprise a carboxylate ion/carboxylic acid mixture, such as a citric acid/citrate or malic acid/malate mixture, and/or may have a pH of from 4 to 6.

In these alternative embodiments, the uranium-230 remains on the resin 2 and is allowed stand to produce more $^{226}$Th by radioactive decay of the $^{230}$U. The resin 2 may be allowed to stand until the $^{226}$Th again achieves equilibrium with the $^{230}$U. Alternatively, the resin 2 may be allowed to stand for a period of time of from 5 to 12 or more $^{226}$Th half-lives (about 30 to 360 minutes), such as from 7 to 12 half-lives (214 to 360 minutes), or from 8 to 11 half-lives (244 to 330 minutes), or about 10 half-lives (about 306 minutes, 5 hours), where a $^{226}$Th half-life is about 30.6 minutes.

After additional thorium-226 is produced, the resin is again contacted with an additional portion of acid 22 to elute additional thorium-226 from the resin 2 to form a second portion of solution 24. The elution process may be repeated one or more times, such as 1, 2, 3, 4, 5 or more times, to separate the $^{226}$Th from the $^{230}$U. In some embodiments, the elution process is performed once or twice daily, and may be performed for up to 10 half-lives of $^{230}$U, such as about 200 days. The elution process may be easily automated.

In any embodiments, the disclosed method may produce a radiochemical yield of $^{226}$Th of from 50% to 99.9%, such as from 60% to 99%, from 70% to 98%, from 80% to 97%, or from 85% to 95%, and in some examples, the method produced $^{226}$Th with a radiochemical yield of 90%. Alternatively, or additionally, the $^{226}$Th produced by the disclosed method may have a radiochemical purity of from 80% to 100%, such as from 85% to 100%, from 90% to 100%, from 95% to 100%, from 97% to 100%, from 98% to 100%, from 99% to 100%, from 99.5% to 100%, from 99.7% to 100%, or from 99.9% to 100%.

The disclosed method also may yield $^{226}$Th with a recovery of parent $^{230}$U for each elution cycle of from 80% to 100%, such as from 85% to 100%, from 90% to 100%, from 95% to 100%, from 97% to 100%, from 98% to 100%, from 99% to 100%, from 99.2% to 100%, or from 99.5% to 100%.

The disclosed $^{230}$U/$^{226}$Th reverse type generator (retention of daughter on resin instead of the parent) has several advantages over other generators where the parent nuclei is maintained on the column and the daughter nuclei is eluted. The benefits of the disclosed generator include a minimal contact time of the alpha emitting radionuclides that results in less destruction to the resin. This in turn helps to minimize potential generator failure. Additionally, by eluting with a citrate buffer, such as a pH 5 citrate buffer, biological molecules can be directly radiolabeled with $^{226}$Th, without a need to first isolate the $^{226}$Th and thus contamination by further decay products is reduced. Furthermore, the column can be routinely and easily replaced and without compromising the integrity of the generator.

III. Examples

Example 1

A. Materials and Methods Materials

Protactinium-230 ($^{230}$Pa) was obtained from Oak Ridge National Laboratory as a side product from the production of $^{225}$AC. Irradiated thorium targets were dissolved in 10M hydrochloric acid spiked with hydrofluoric acid and then contacted with an anion exchange column (AG1-X8, Bio-rad). Protactinium-230 was then eluted with 4M hydrochloric acid. Chloride resin, an extraction chromatography resin (TrisKem), was used to purify $^{230}$U from its parent isotope $^{230}$Pa. DGA resin (Eichrom) was used in the implementation of the $^{230}$U/$^{226}$Th generator. All syringes used were non-sterile with a luer lok adaptor (Norm-ject) unless stated otherwise. All chemicals used were trace metal basis.

B. 230U/226Th Generator Design

A small 1 mL column (Chromabond) was used as the column for the generator. Approximately 100 mg of DGA resin was added to the column, and a small frit was used to compact the resin into the column. For the addition of solutions to the column, luer lok syringes were used with an adaptor for the column. Before use, the column was washed with ~10 mL milli-Q water and then equilibrated with 1 mL concentrated HCl.

Uranium-230 and its decay product $^{226}$Th were first sorbed onto 100 mg of DGA resin with 5 mL of 6 M hydrochloric acid. Uranium-230 was then eluted in 5 mL of 0.1 M nitric acid as $^{226}$Th remained sorbed. After elution of the $^{230}$U, $^{226}$Th was eluted from the resin in 1 mL 0.1 M citric acid, pH 5. The column was then washed with 10-20 mL milli-Q water and then equilibrated with 1 mL concentrated hydrochloric acid. Once the daughter, $^{226}$Th, reached equilibrium with the parent isotope $^{230}$U in the nitric acid solution, 5 mL of concentrated hydrochloric acid was added to the 5 mL $^{230}$U solution. This solution was once again passed through the DGA resin and both $^{226}$Th and $^{230}$U were sorbed onto the column. The above elution process was then repeated to obtain additional $^{226}$Th in 1 mL 0.1 M citric acid, pH 5. FIG. 1 provides a flow chart of the method used.

Alternatively, a solution of $^{230}$U and its decay product $^{226}$Th in 2 M HCl are sorbed onto a column containing TRU resin (Eichrom). Under these conditions, the $^{230}$U binds to the resin, while $^{226}$Th is eluted with 2M HCl. Thorium-226 is then eluted every 5 hours. In order to obtain the thorium in a form amenable to labeling, the $^{226}$Th eluent from this column is loaded on to a small column containing a cation exchange resin, such as Bio-rad AG® 50WX8, which binds $^{226}$Th. The $^{226}$Th is then eluted with 0.1 M Citrate pH 5 for use, for example, in bioconjugation.

C. Results

In both examples, the $^{230}$U/$^{226}$Th generator yielded $^{226}$Th with a >99.5% recovery of parent $^{230}$U for each elution cycle. A radiochemical yield of approximately 90% was obtained for $^{226}$Th removal from the DGA resin with high radiochemical purity (>99.9%). Multiple elutions, implemented once or twice daily, were performed successfully with substantially consistent radiochemical yields and purities.

D. Conclusion

A dual generator concept was successfully designed to provide a dependable supply of $^{226}$Th. The $^{230}$U/$^{226}$Th generator, in turn, provides $^{226}$Th in high radiochemical yield and purity and in a form that is amenable to direct labeling with chelates for use in, for example, targeted alpha therapy.

Example 2

The Effect of pH on $^{226}$Th Elution

Figure 3:
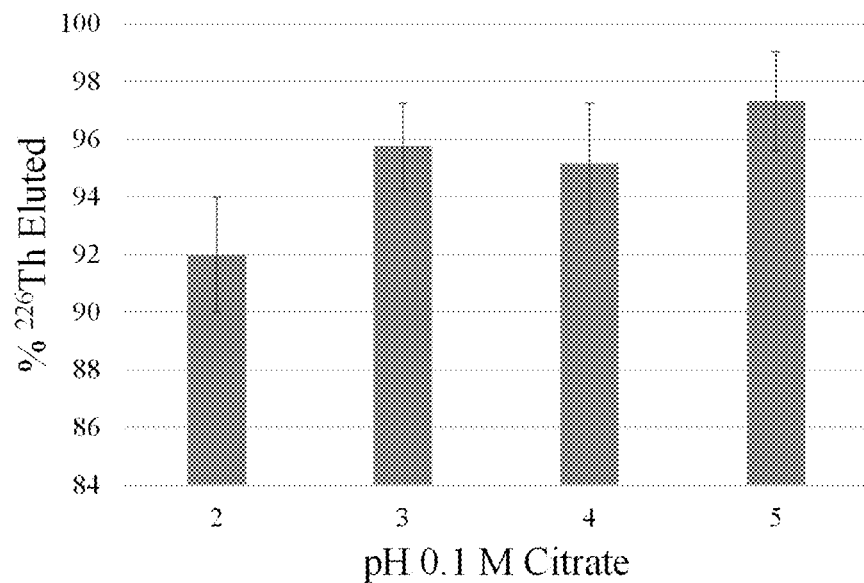
FIG. 3 is a graph of percentage of $^{226}$Th eluted versus pH of the 0.1 M citrate buffer, illustrating how the amount of $^{226}$Th eluted varies with pH.

In a study, a mixture of $^{230}$U and $^{226}$Th were loaded onto a column as described in Example 1. After elution of the $^{230}$U, $^{226}$Th was eluted from the resin using a citric acid buffer at various pH levels, such as pH 2, 3, 4 and 5. FIG. 3 provides the results. As FIG. 3 illustrates, greater than 90% of the $^{226}$Th was eluted at all pH values tested. However, 0.1 M citrate buffer at pH 5 resulted in greater than 96% elution of the $^{226}$Th, and this buffer was used for subsequent tests.

Example 3

$^{226}$Th Elution Profile

Figure 4:
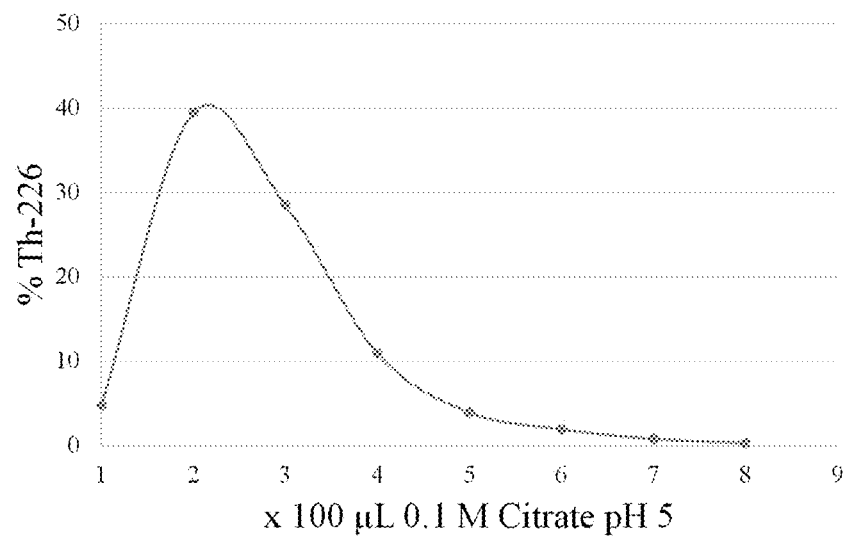
FIG. 4 is a graph of percentage of $^{226}$Th eluted versus volume buffer used, illustrating the elution profile of the $^{226}$Th in 0.1 M citrate buffer at pH 5.

Using 0.1 M citrate buffer at pH 5, the elution profile of $^{226}$Th was investigated by measuring the elution at 100 μL intervals. FIG. 4 provides the resulting elution profile. FIG. 4 demonstrates that there was greater than 90% elution of the $^{226}$Th at 500 μL, and greater than 99% elution with 1 mL of buffer.

Example 4

$^{230}$U/$^{226}$Th Generator Evaluation

Figure 5:
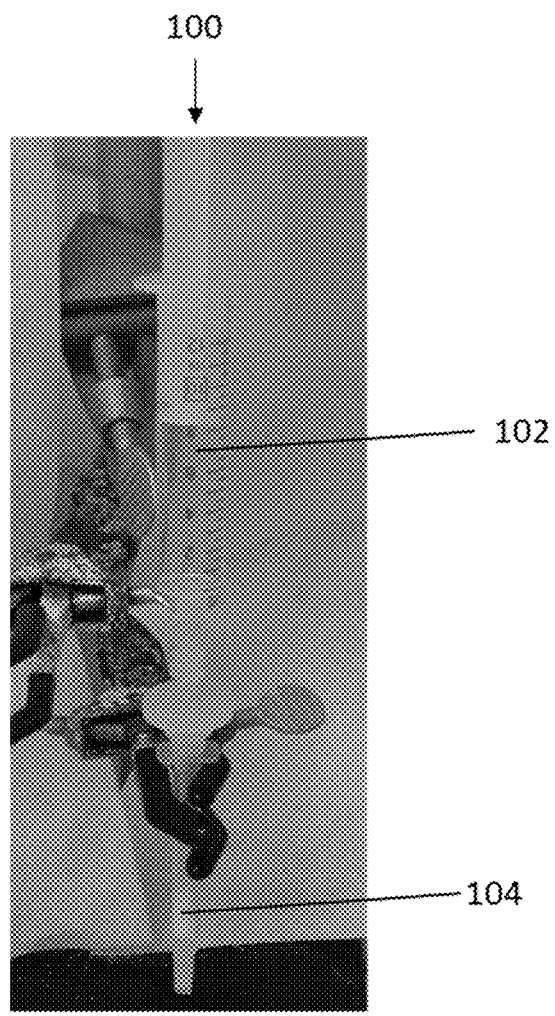
FIG. 5 is a digital image illustrating one exemplary embodiment of an apparatus suitable to elute thorium-226 using the disclosed method.
Figure 6:
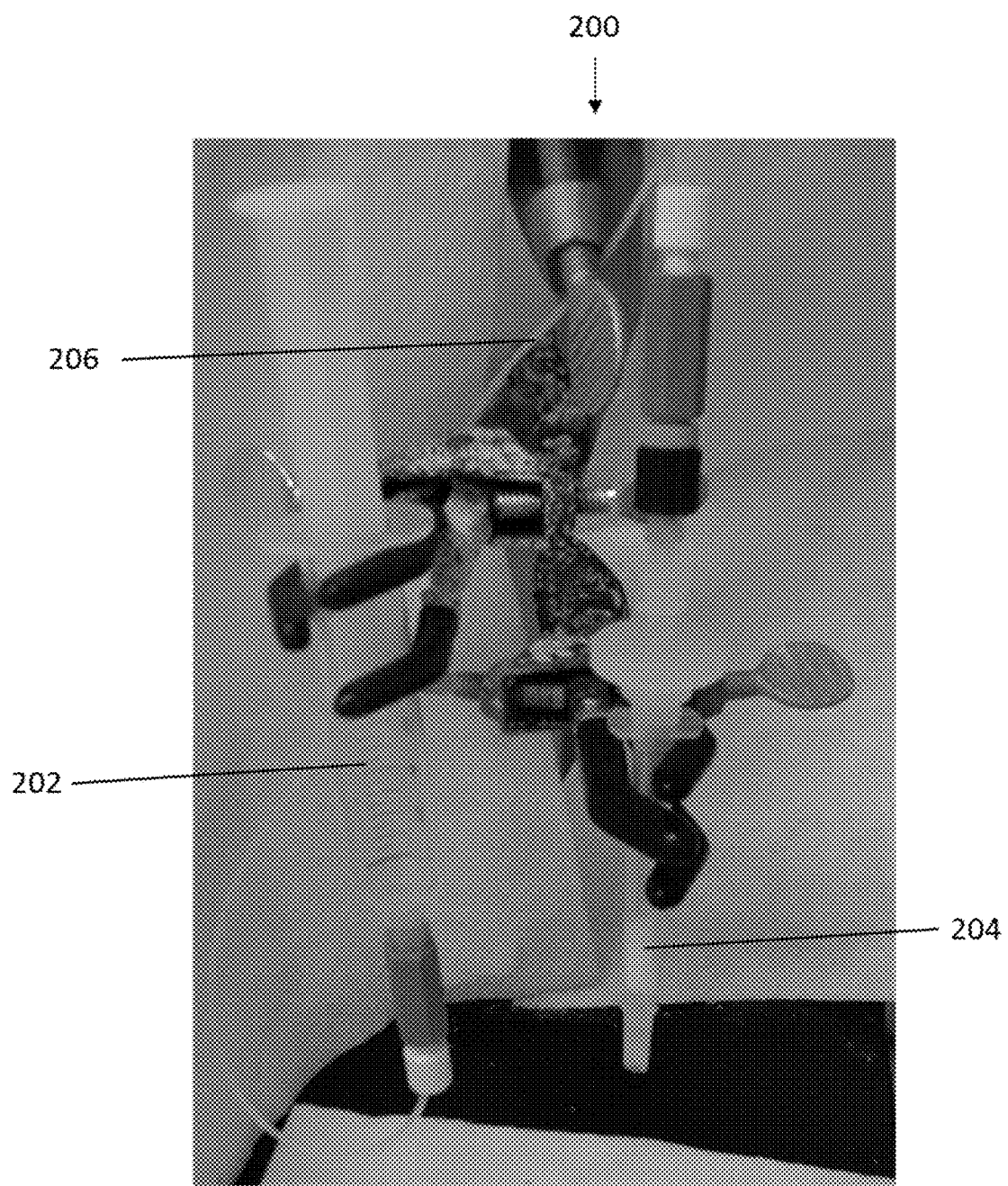
FIG. 6 is a digital image illustrating an alternative exemplary embodiment of an apparatus suitable to elute thorium-226 using the disclosed method.

The $^{230}$U/$^{226}$Th radionuclide generator was evaluated for 60 days (about 3 half-lives of $^{230}$U). Loading breakthrough, quantity of $^{230}$U in eluted $^{226}$Th product and % yield of $^{226}$Th were evaluated. Two exemplary generator set-ups were evaluated. FIGS. 5 and 6 provide digital images of the two set-ups. FIG. 5 shows device 100 (configuration 1) that comprises a syringe 102 directly attached to column 104. FIG. 6 shows device 200 (configuration 2) that comprises syringe 202 connected to column 204 by line 206. Without being bound to a particular theory, line 206 in device 200 may provide additional back-pressure and/or better control of the flow rate.

Figure 7:
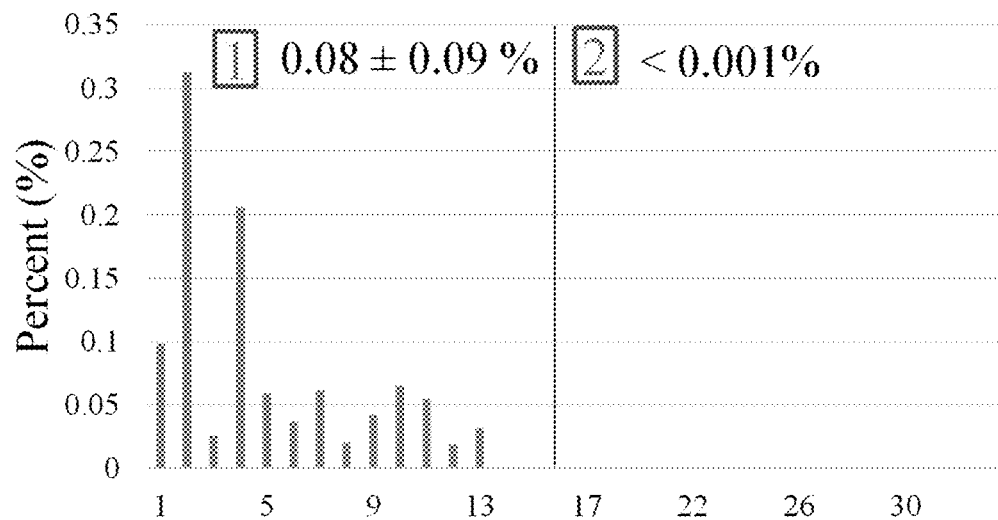
FIG. 7 is a graph of percent $^{230}$U versus fraction number, comparing the loading breakthrough for each of the apparatuses illustrated in FIG. 5 (labeled 1) and FIG. 6 (labeled 2).
Figure 8:
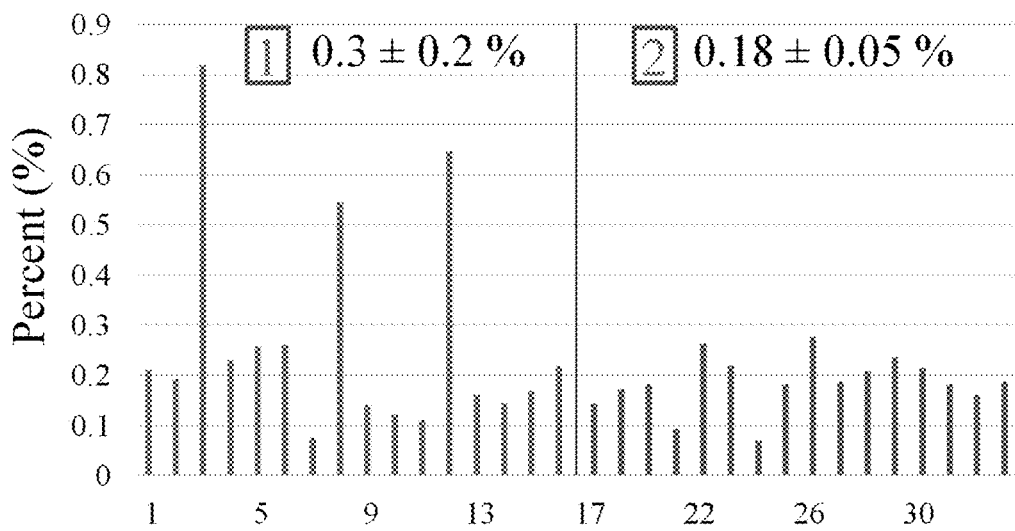
FIG. 8 is a graph of percent $^{230}$U versus fraction number, comparing the amounts of uranium-230 in each thorium-226 fraction from the apparatuses illustrated in FIG. 5 (labeled 1) and FIG. 6 (labeled 2).
Figure 9:
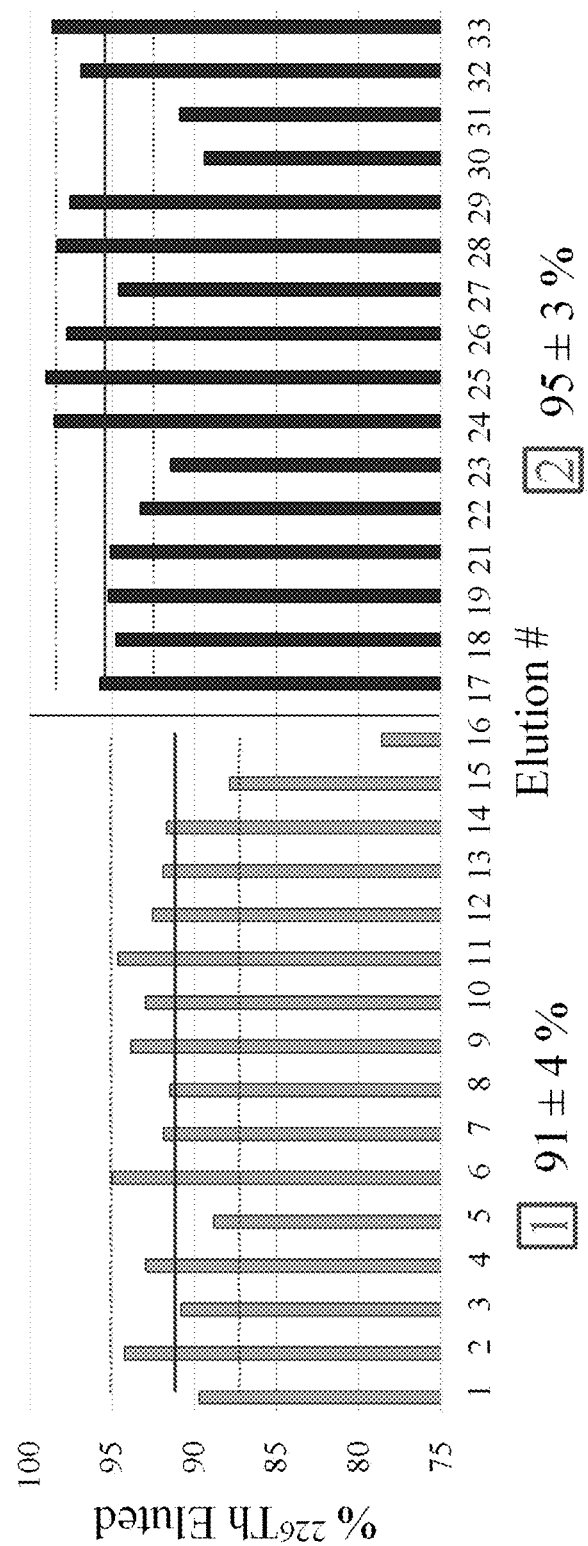
FIG. 9 is a graph of percent $^{226}$Th eluted versus fraction number, comparing the elution efficiencies of the apparatuses shown in FIG. 5 (labeled 1) and FIG. 6 (labeled 2).

FIGS. 7-9 provide loading breakthrough, $^{230}$U content in $^{226}$Th fraction, and $^{226}$Th elution efficiency data for device 100 (illustrated by '1' in FIGS. 7-9) and device 200 (illustrated by '2' in FIGS. 7-9). FIG. 7 provides data illustrating the loading breakthrough, i.e., the amount of $^{230}$U that was eluted while the column was being loaded, was 0.08±0.09% for device 100, but was below detection limits (<0.001%) for device 200.

The amount of $^{230}$U that remained on the column and therefore eluted with the $^{226}$Th product was 0.3±0.2% for device 100 and 0.18±0.05% for device 200 (FIG. 8). And the percent of $^{226}$Th that eluted from the column (decay corrected) was 91±4% for device 100 and 95±3% for device 200 (FIG. 9). These data show that increased control over the flow rate may result in improved yields and lower breakthrough.

The $^{230}$U/$^{226}$Th generator and method disclosed within successfully supplies $^{226}$Th routinely over a 60 day period. Benefits to this reverse type generator (retention of daughter on resin instead of the parent) are the minimal contact time of the alpha emitting radionuclides resulting in less destruction to resin minimizing potential generator failure and elution in pH 5, which allows for direct radiolabeling of biological molecules with $^{226}$Th. Additionally, the column can be replaced routinely and easily without compromising the integrity of the generator.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method, comprising:
   forming a first solution comprising uranium-230 and thorium-226;
   contacting a first resin with the first solution such that the uranium-230 and the thorium-226 bind to the first resin, wherein the first resin is a diglycolamide resin, a monoamide resin, a malonamide resin, or a multi-podant DGA ligand,
   eluting the thorium-226 from the first resin with a carboxylic acid-based chelating buffer to form a second solution comprising the thorium-226 and the carboxylic acid-based chelating buffer.

2. The method of claim 1, wherein the first solution comprises a first mineral acid having a first acid concentration of from greater than 2 M to 12 M.

3. The method of claim 2, wherein the first mineral acid is hydrochloric acid, hydrofluoric acid, hydrobromic acid, hydriodic acid sulfuric acid, nitric acid, phosphoric acid, or a combination thereof.

4. The method of claim 1, wherein the first resin is N,N,N',N'-tetra-n-octyldiglycolamide, or N,N,N',N'-tetrakis-2-ethylhexyldiglycolamide.

5. The method of claim 1, wherein prior to eluting the thorium-226 the method comprises eluting the uranium-230 from the first resin with a second mineral acid to form a third solution.

6. The method of claim 5, wherein the second mineral acid is nitric acid.

7. The method of claim 5, wherein the second mineral acid has a second acid concentration of from greater than zero to less than 6M.

8. The method of claim 5, further comprising:
   allowing the third solution to stand for a time period sufficient for a portion of the uranium-230 in the third solution to decay to form additional thorium-226;
   adding the third solution to the first resin; and
   eluting the additional thorium-226 with an additional amount of the chelating buffer.

9. The method of claim 8, wherein the time period is from 30 to 360 minutes.

10. A method, comprising:
    forming a first solution comprising uranium-230 and thorium-226;
    contacting a first resin selected from a phosphonic acid resin, a phosphine oxide resin, or a phosphine sulfide resin with the first solution such that the uranium-230 and the thorium-226 bind to the first resin;
    eluting the thorium-226 from the first resin with a mineral acid to form a second solution, the mineral acid having an acid concentration of from 0.5 M to 4 M;
    contacting a cation exchange resin with the second solution; and
    eluting the thorium-226 from the cation exchange resin with the chelating buffer to form a third solution.

11. The method of claim 10, further comprising allowing the first resin and uranium-230 to stand for a time period sufficient for a portion of the uranium-230 on the first resin to decay to form additional thorium-226, and eluting the additional thorium-226 from the first resin with an additional amount of the mineral acid.

12. The method of claim 11, wherein the time period is from 30 to 360 minutes.

13. The method of claim 1, wherein the chelating buffer comprises a carboxylic acid, a hydroxyl group, or a combination thereof.

14. The method of claim 13, wherein the chelating buffer comprises glycolic acid, citric acid, tartaric acid, malonic acid, oxalic acid, succinic acid, glutaric acid, adipic acid, isocitric acid, aconitric acid, propane-1,2,3-tricarboxylic acid, malic acid, maleic acid, lactic acid, or a combination thereof.

15. The method of claim 13, wherein the chelating buffer has a pH of from 0 to 8.

16. A method, comprising:
    forming a first solution comprising uranium-230 and thorium-226 in 6M hydrochloric acid;
    contacting a diglycolamide resin with the first solution to bind the uranium-230 and thorium-226 to the resin;
    eluting the uranium-230 from the resin with nitric acid having a nitric acid concentration of from 0.01 M to 0.25 M, to form a second solution comprising uranium-230;
    eluting the thorium-226 from the resin with a chelating buffer to form a third solution comprising thorium-226, the chelating buffer comprising a carboxylic acid and having a pH of from 2 to 6.

17. The method of claim 16, wherein the chelating buffer comprises citric acid.

18. The method of claim 10, comprising:
    forming the first solution comprising uranium-230 and thorium-226 in 6M hydrochloric acid;
    contacting the first resin with the first solution to bind the uranium-230 and thorium-226 to the first resin;
    eluting the thorium-226 from the first resin with a first portion of hydrochloric acid having an acid concentration of from 0.5 M to 4 M to form the second solution;
    contacting the cation exchange resin with the second solution; and
    eluting the thorium-226 from the cation exchange resin with the chelating buffer to form the third solution comprising thorium-226, wherein the chelating buffer comprises a carboxylic acid and has a pH of from 4 to 6.

19. The method of claim 18, wherein the chelating buffer comprises citric acid.

* * * * *